(12) United States Patent
Tegels

(10) Patent No.: US 11,071,539 B2
(45) Date of Patent: Jul. 27, 2021

(54) THREE SUTURE LARGE BORE CLOSURE DEVICE AND METHODS

(71) Applicant: St. Jude Medical Puerto Rico LLC, Caguas, PR (US)

(72) Inventor: Zachary J. Tegels, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 296 days.

(21) Appl. No.: 16/164,477

(22) Filed: Oct. 18, 2018

(65) Prior Publication Data

US 2019/0046179 A1 Feb. 14, 2019

Related U.S. Application Data

(63) Continuation of application No. 13/794,425, filed on Mar. 11, 2013, now Pat. No. 10,136,885.

(51) Int. Cl.
*A61B 17/04* (2006.01)
*A61B 17/00* (2006.01)
*A61B 17/06* (2006.01)

(52) U.S. Cl.
CPC ...... *A61B 17/0469* (2013.01); *A61B 17/0057* (2013.01); *A61B 17/0482* (2013.01);
(Continued)

(58) Field of Classification Search
CPC ............ A61B 17/0057; A61B 17/0469; A61B 17/0482; A61B 17/0485;
(Continued)

(56) References Cited

U.S. PATENT DOCUMENTS

| 3,470,875 A | 10/1969 | Johnson |
| 5,431,666 A | 7/1995 | Sauer et al. |

(Continued)

FOREIGN PATENT DOCUMENTS

| EP | 0818178 A2 | 1/1998 |
| EP | 1158907 A1 | 12/2001 |

(Continued)

OTHER PUBLICATIONS

Notification of Transmittal of the International Search Report and the Written Opinion of the International Searching Authority, or the Declaration for International Application No. PCT/US2012/064768, dated Feb. 19, 2013, (18 pp.).

(Continued)

*Primary Examiner* — Diane D Yabut
*Assistant Examiner* — Christian D Knauss
(74) *Attorney, Agent, or Firm* — Dorsey & Whitney LLP

(57) ABSTRACT

A vascular closure device includes an anchor, a suture carrying portion, and at least three needles. The anchor is positionable through a vessel puncture in a vessel wall and operable between expanded and retracted positions. The suture carrying portion is positioned distal of the anchor and configured to carry at least one suture. The needles are operable between an advanced position extending through the vessel wall adjacent to the vessel puncture to connect to the at least one suture, and a retracted position in which the needles position the at least one suture through the vessel wall. The needles and sutures are configurable to close large bore openings in the vessel wall.

18 Claims, 13 Drawing Sheets

(52) U.S. Cl.
CPC ........... *A61B 2017/00663* (2013.01); *A61B 2017/0472* (2013.01); *A61B 2017/06042* (2013.01)

(58) Field of Classification Search
CPC .. A61B 2017/00663; A61B 2017/0472; A61B 2017/0488; A61B 17/06004; A61B 2017/06042
See application file for complete search history.

(56) References Cited

U.S. PATENT DOCUMENTS

| | | | |
|---|---|---|---|
| 5,507,755 A | 4/1996 | Gresl et al. |
| 5,520,702 A | 5/1996 | Sauer et al. |
| 5,562,686 A | 10/1996 | Sauer et al. |
| 5,613,974 A | 3/1997 | Andreas et al. |
| 5,643,292 A | 7/1997 | Hart |
| 5,674,231 A | 10/1997 | Green et al. |
| 5,700,273 A | 12/1997 | Buelna et al. |
| 5,709,692 A | 1/1998 | Mollenauer et al. |
| 5,728,114 A | 3/1998 | Evans et al. |
| 5,766,183 A | 6/1998 | Sauer |
| 5,836,955 A | 11/1998 | Buelna et al. |
| 5,860,990 A | 1/1999 | Nobles et al. |
| 5,954,732 A | 9/1999 | Hart et al. |
| 5,972,005 A | 10/1999 | Stalker et al. |
| 6,036,699 A | 3/2000 | Andreas et al. |
| 6,048,357 A | 4/2000 | Kontos |
| 6,059,800 A | 5/2000 | Hart et al. |
| 6,136,010 A | 10/2000 | Modesitt et al. |
| 6,143,004 A | 11/2000 | Davis et al. |
| 6,355,050 B1 | 3/2002 | Andreas et al. |
| 6,562,052 B2 | 5/2003 | Nobles et al. |
| 6,623,509 B2 | 9/2003 | Ginn |
| 6,641,592 B1 | 11/2003 | Sauer et al. |
| 6,896,692 B2 | 5/2005 | Ginn et al. |
| 6,911,034 B2 | 6/2005 | Nobles et al. |
| 6,932,824 B1 | 8/2005 | Roop et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,083,635 B2 | 8/2006 | Ginn |
| 7,235,087 B2 | 6/2007 | Modesitt et al. |
| 7,361,183 B2 | 4/2008 | Ginn |
| 7,390,328 B2 | 6/2008 | Modesitt |
| 7,553,319 B2 | 6/2009 | Bagaoisan et al. |
| 7,601,161 B1 | 10/2009 | Nobles et al. |
| 7,621,937 B2 | 11/2009 | Pipenhagen et al. |
| 7,686,821 B2 | 3/2010 | Hathaway et al. |
| 7,731,726 B2 | 6/2010 | Belhe et al. |
| 7,744,610 B2 | 6/2010 | Hausen |
| 7,752,853 B2 | 7/2010 | Singh et al. |
| 7,753,933 B2 | 7/2010 | Ginn et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,985,240 B2 | 7/2011 | Bagaoisan et al. |
| 8,029,476 B2 | 10/2011 | Rosenberg et al. |
| 8,048,092 B2 | 11/2011 | Modesitt et al. |
| 8,083,768 B2 | 12/2011 | Ginn et al. |
| 8,192,456 B2 | 6/2012 | Holman et al. |
| 2005/0085854 A1 | 4/2005 | Ginn |
| 2006/0212071 A1 | 9/2006 | Ginn et al. |
| 2008/0065151 A1 | 3/2008 | Ginn |
| 2009/0099578 A1 | 4/2009 | Heneveld et al. |
| 2009/0306685 A1 | 12/2009 | Fill |
| 2010/0042118 A1 | 2/2010 | Garrison et al. |
| 2011/0071567 A1 | 3/2011 | Modesitt et al. |
| 2012/0053600 A1 | 3/2012 | Fortson |
| 2012/0296373 A1* | 11/2012 | Roorda .............. A61B 17/0057 606/213 |
| 2013/0123812 A1 | 5/2013 | Tegels |
| 2013/0144316 A1 | 6/2013 | McCrea et al. |
| 2013/0325058 A1* | 12/2013 | Roorda .............. A61B 17/0469 606/213 |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 A1 | 2/1997 |
| WO | 0051498 A1 | 9/2000 |
| WO | 0078226 A1 | 12/2000 |
| WO | 2010081106 A1 | 7/2010 |

OTHER PUBLICATIONS

Notification of Transmittal of the International Search Report and the Written Opinion of the International Searching Authority, or the Declaration for International Application No. PCT/US2012/064770, dated Feb. 19, 2013, (16 pp.).

Notification of Transmittal of the International Search Report and the Written Opinion of the International Searching Authority, or the Declaration for International Application No. PCT/US2012/066012, dated Feb. 19, 2013, (17 pp.).

PCT Communication Relating to the Results of the Partial International Search for International Application No. PCT/US2012/041196, dated Sep. 11, 2012.

* cited by examiner

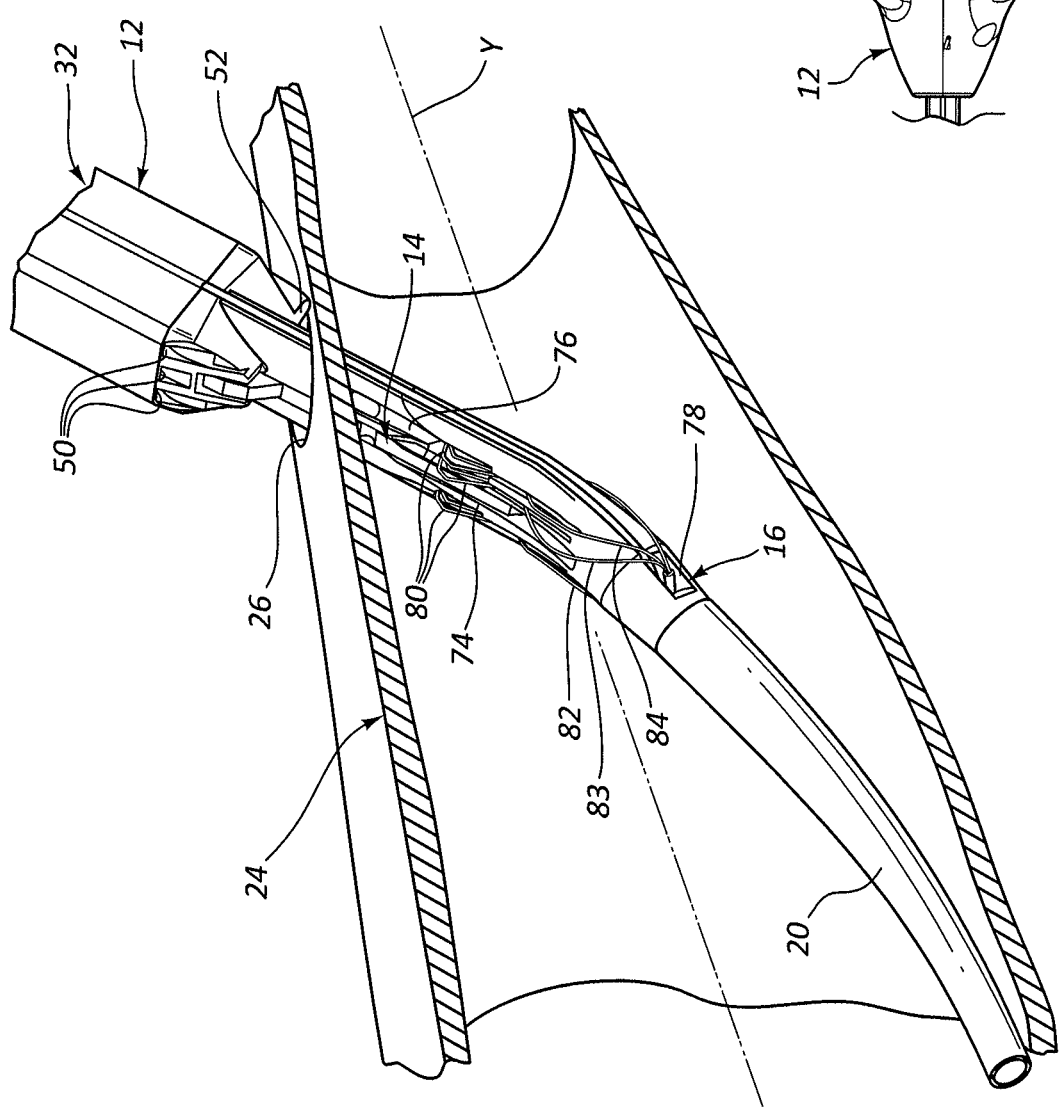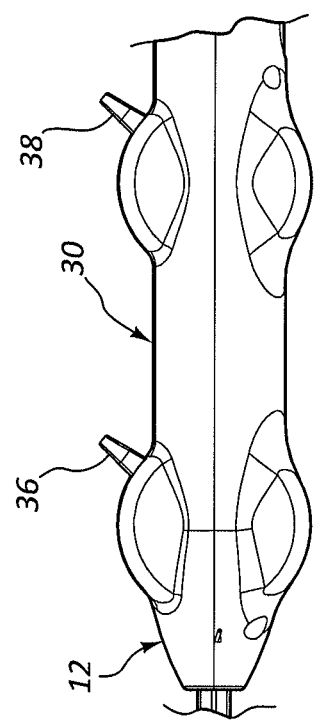

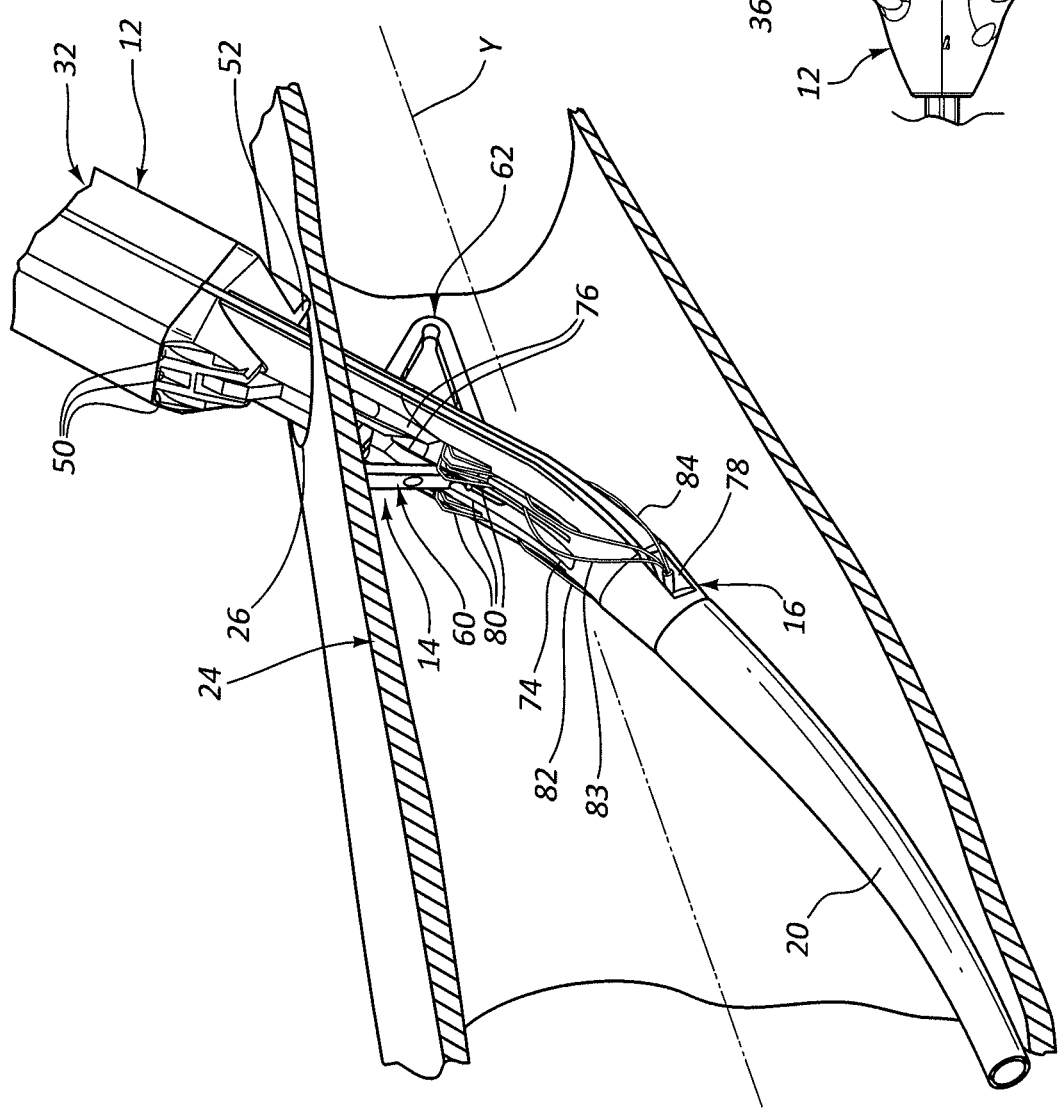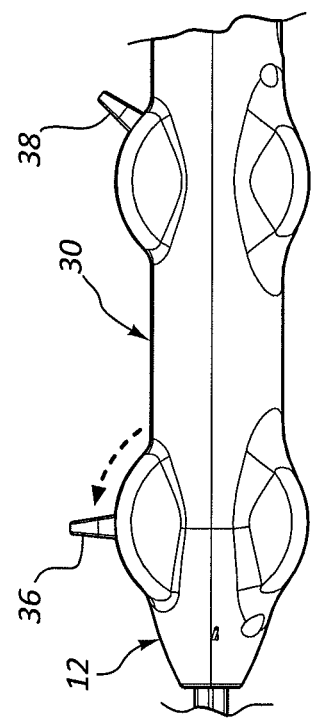
FIG. 4A
FIG. 4B

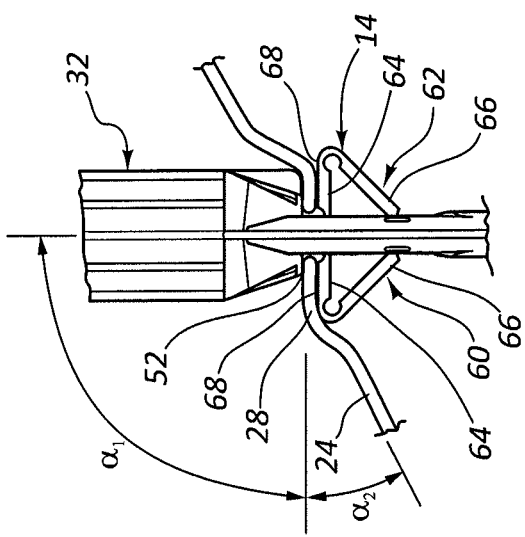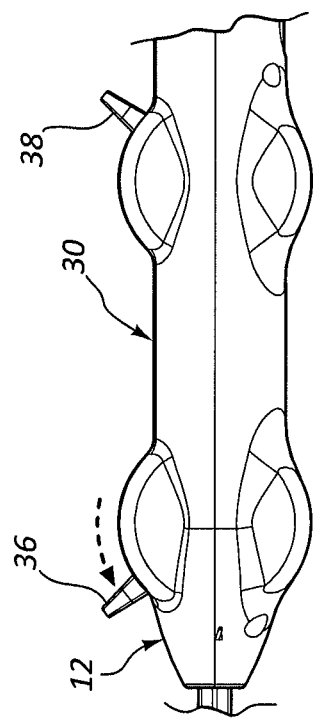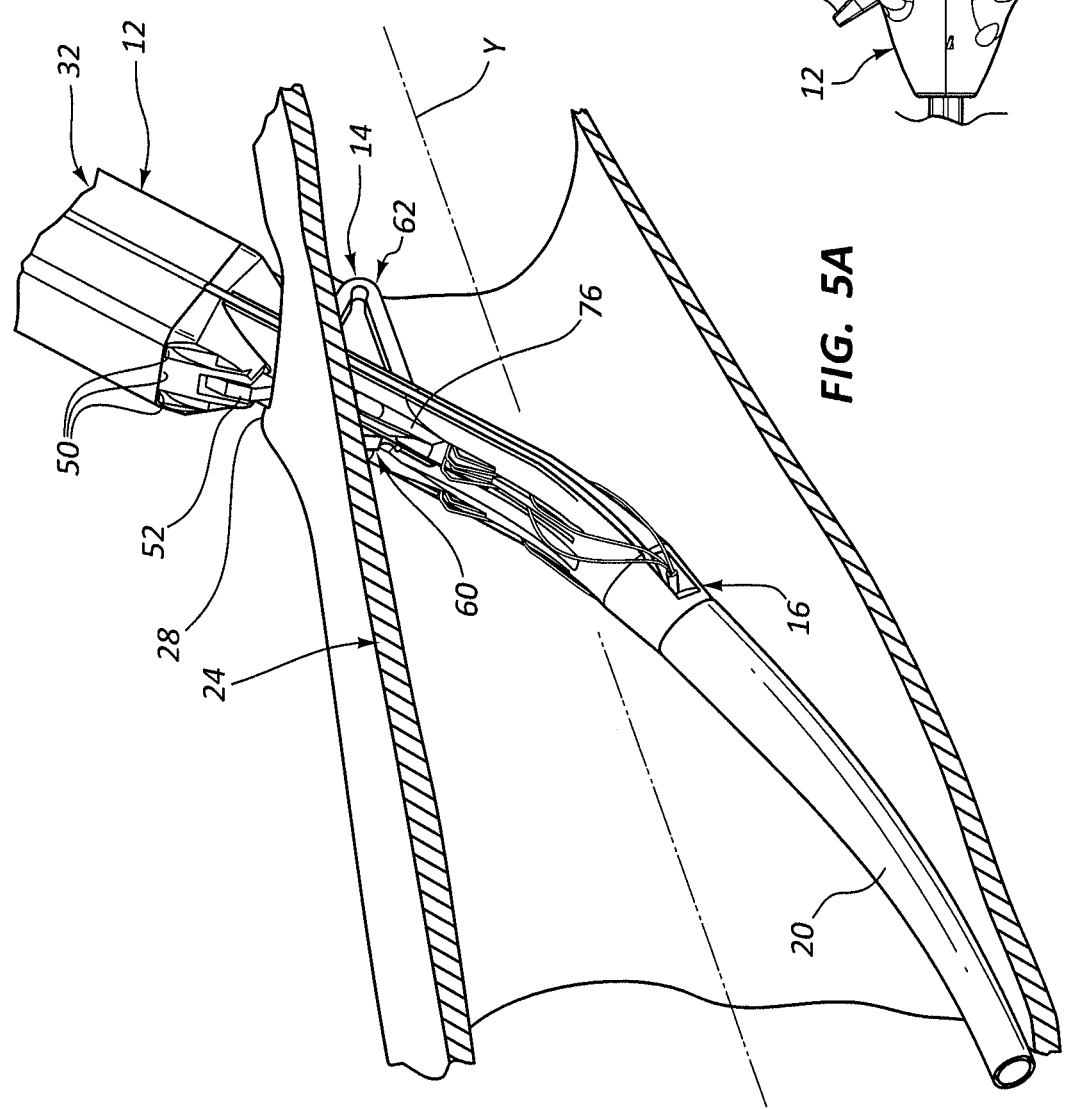

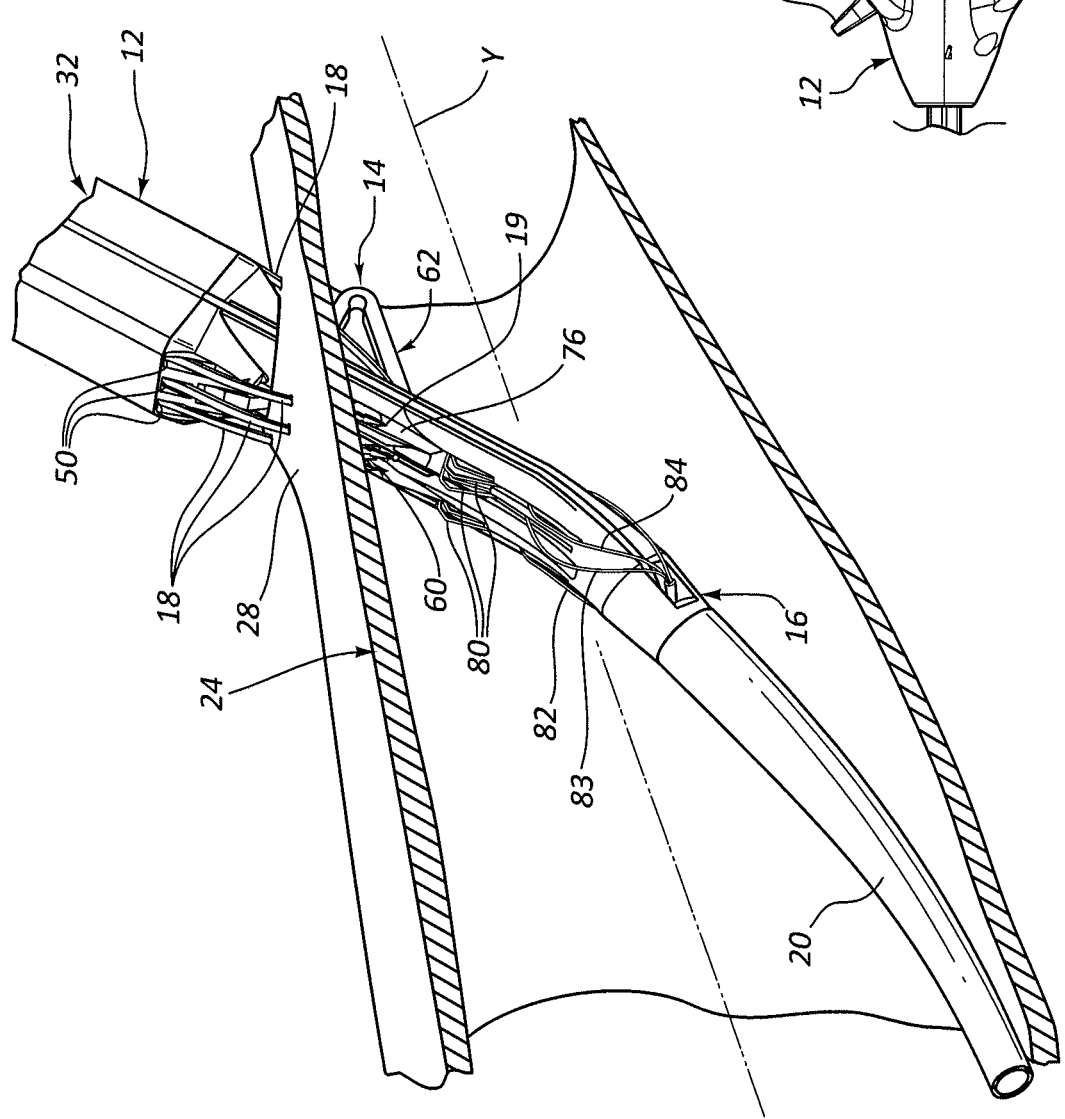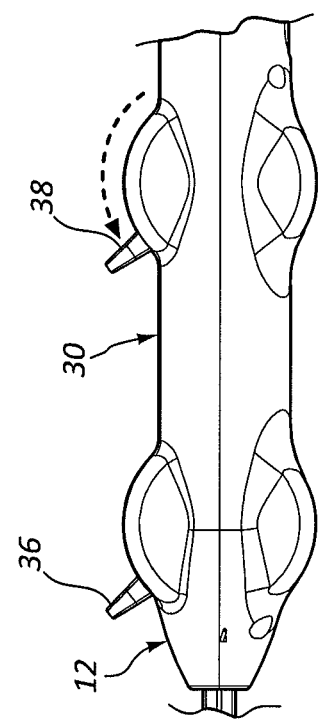
FIG. 6A
FIG. 6B

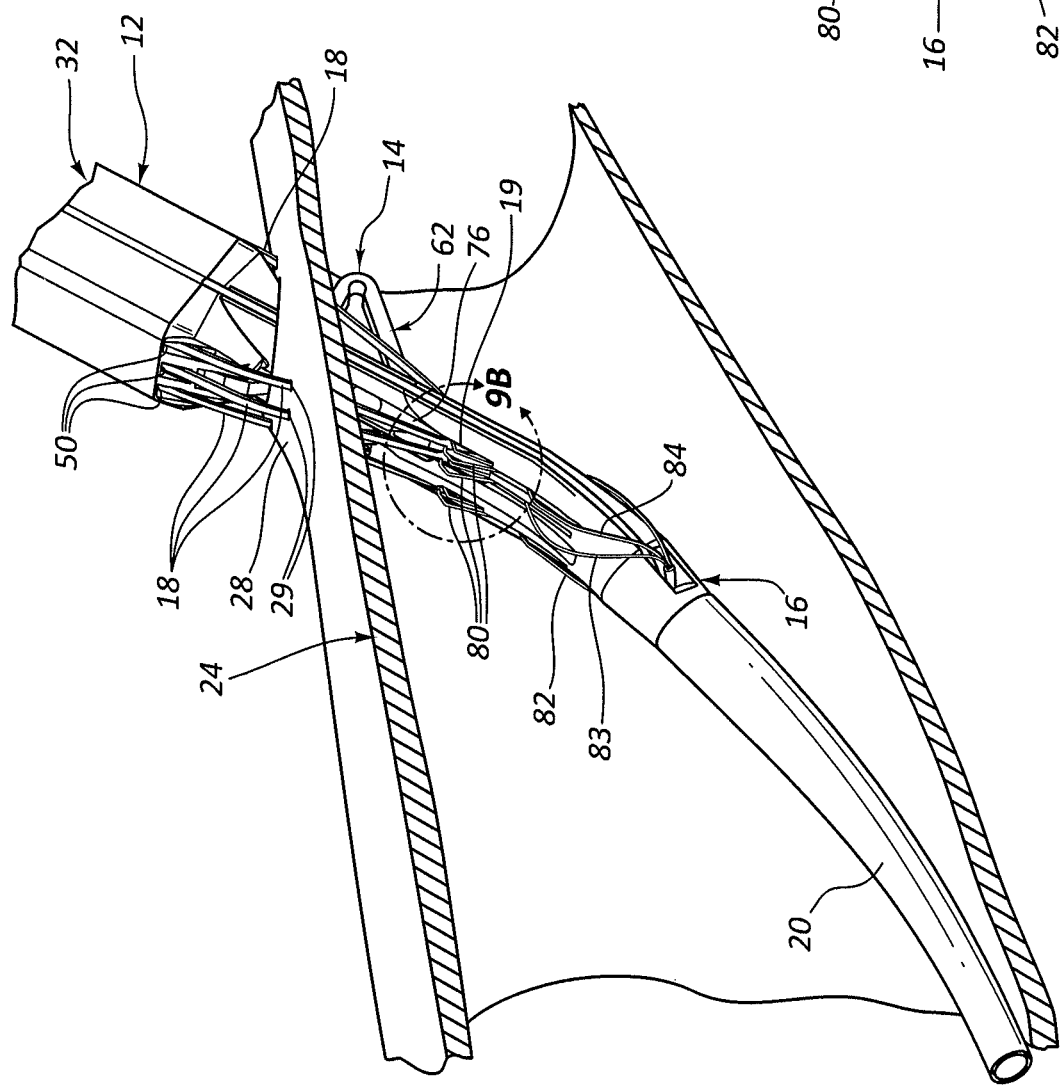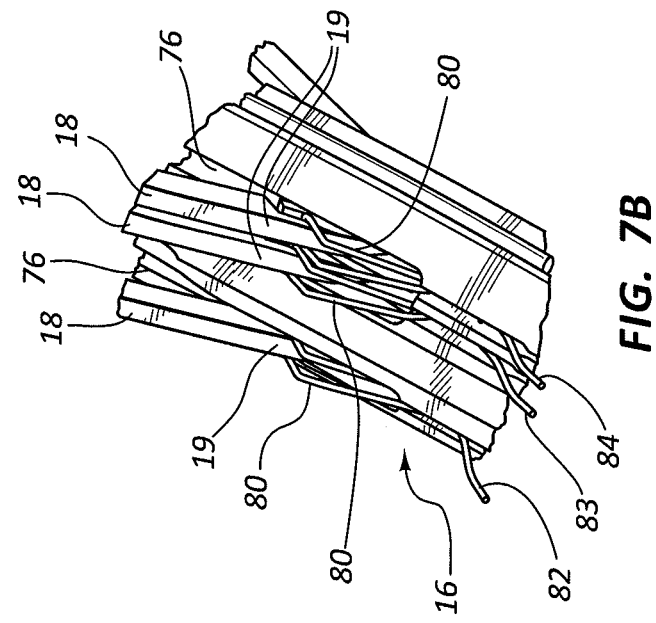

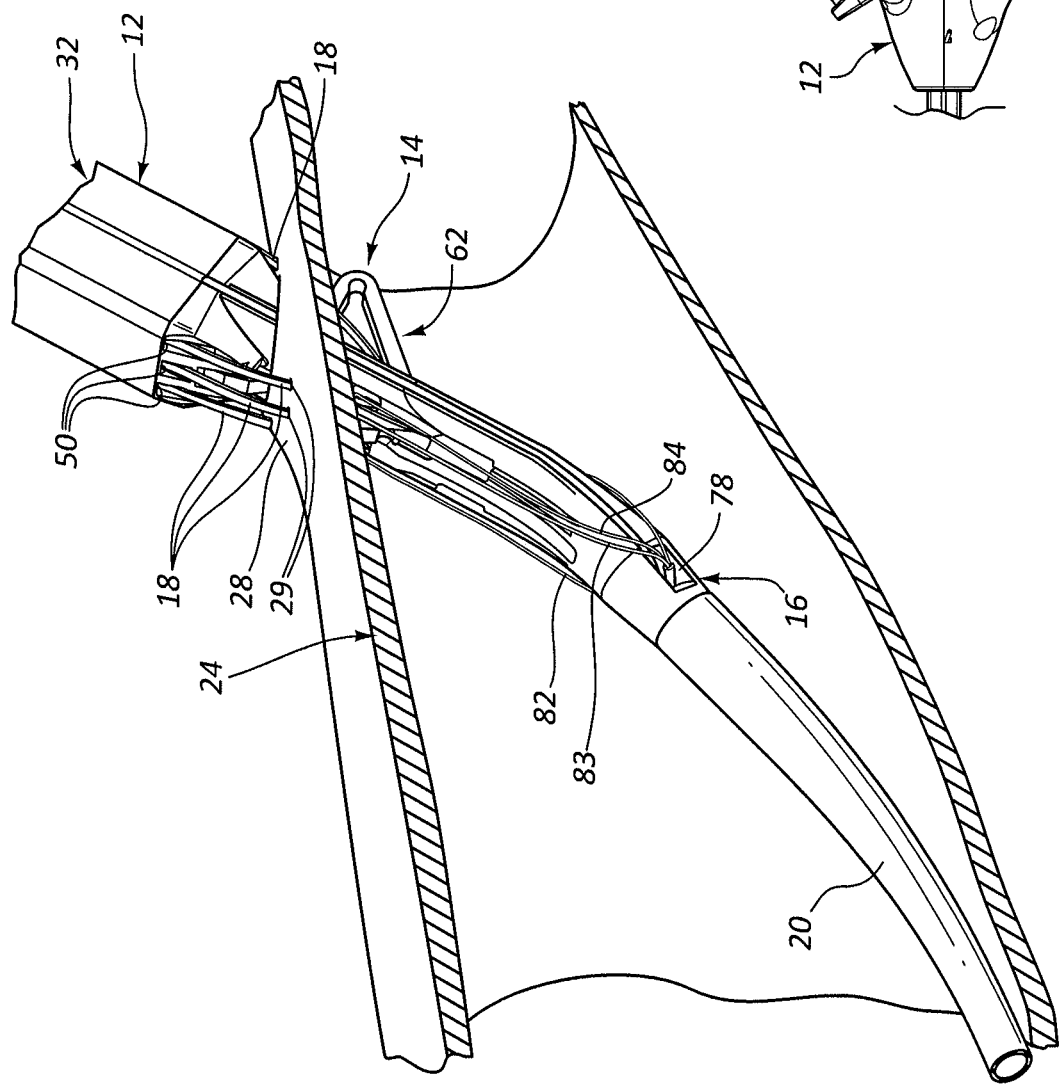
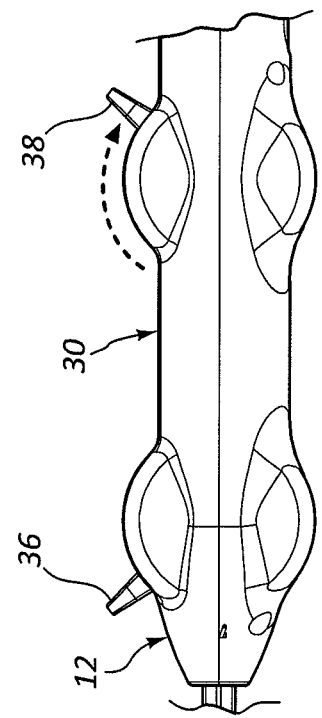
FIG. 8A
FIG. 8B

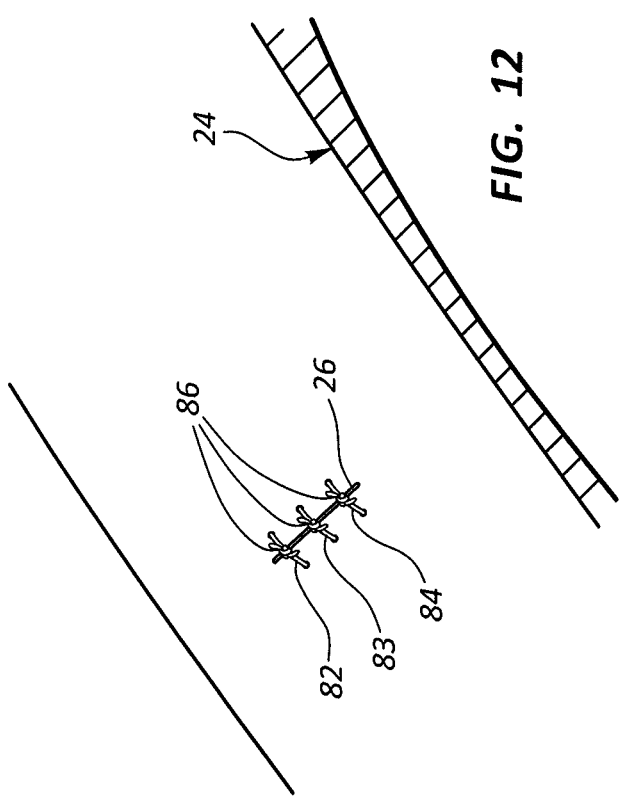
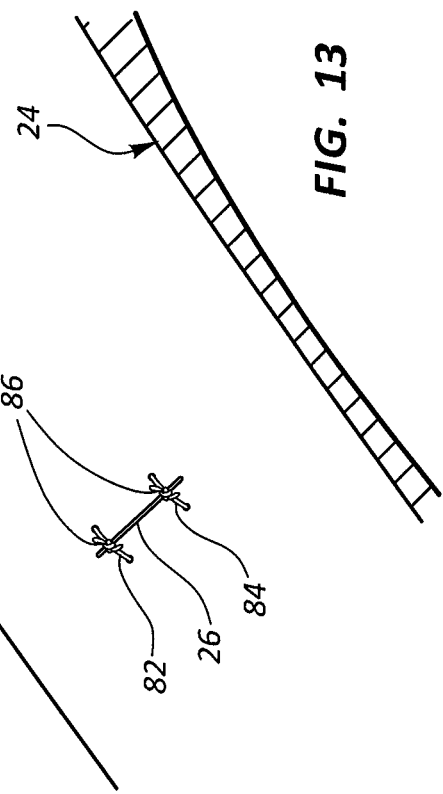

THREE SUTURE LARGE BORE CLOSURE DEVICE AND METHODS

RELATED APPLICATION

This is a continuation of U.S. patent application Ser. No. 13/794,425, filed on 11 Mar. 2013, now pending, the disclosure of which is incorporated, in its entirety, by this reference.

TECHNICAL FIELD

The present disclosure relates to closure devices, and more specifically relates to closure devices that place sutures across an opening in a vessel wall.

BACKGROUND

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall.

SUMMARY

One aspect of the present disclosure relates to a vascular closure device including an anchor, a suture carrying portion, and a plurality of needles. The anchor is positionable through a vessel puncture in a vessel wall and operable between expanded and contracted positions. The suture carrying portion is positioned distal of the anchor and configured to carry at least one suture. The plurality of needles are operable between an advanced position extending through the vessel wall adjacent to the vessel puncture to connect to the at least one suture, and a retracted position in which the plurality of needles positions the at least one suture through the vessel wall. At least one of the plurality of needles extends through an aperture in the anchor when in the advanced position.

Two of the plurality of needles may extend through separate apertures in the anchor. The plurality of needles may include at least three pairs of needles. The plurality of needles may include at least first and second pairs of needles, wherein the first pair of needles extends through the anchor. The at least one suture may include three separate sutures. The plurality of needles may include first and second pairs of needles positioned on opposing sides of the anchor. The vascular closure device may include a body portion, wherein the plurality of needles are positioned in the body portion when in the retracted position, and the anchor holds the vessel wall against a distal surface of the body portion when the anchor is in the expanded position.

A further aspect of the present disclosure relates to a vascular closure device that includes a body portion, an anchor, at least three sutures, and three pairs of needles. The anchor is positioned distal of the body portion. The at least three sutures include portions thereof positioned distal of the anchor. The three pairs of needles are carried by the body portion. The three pairs of needles are operable to advance through a vessel wall, connect to the portions of the at least three sutures, and retract to pull the at least three sutures through the vessel wall.

The anchor may be operable between retracted and expanded positions to capture the vessel wall between the anchor and the body portion. At least one of the three pairs of needles may extend through a portion of the anchor. At least one of the three pairs of needles may extend through multiple portions of the anchor. The anchor may include first and second arms extending radially outward when the anchor is in an expanded position, and separate needles may extend through each of the first and second arms. Each of the first and second arms may include a single length of material having a bend along its length. The anchor may be insertable through a puncture in a vessel wall, and the sutures may extend across the puncture after the three pairs of needles are retracted and the vascular closure device is withdrawn from the puncture. The three pairs of needles may be arranged in series. A first needle of each pair of needles may be arranged on one side of a puncture in the vessel wall, and a second of each pair of needles may be arranged on an opposite side of the puncture.

Another aspect of the present disclosure relates to a method of placing sutures in a vessel wall. The method includes providing a suture placement device having a body portion, an anchor, a plurality of needles, and a plurality of sutures. The method may further include inserting the anchor and plurality of sutures through a puncture in the vessel wall, operating the anchor into an expanded position to capture the vessel wall between the body portion and the anchor, advancing the plurality of needles through the vessel wall adjacent to the puncture into engagement with the plurality of sutures, wherein at least one of the plurality of needles extend through the anchor, and retracting the plurality of needles to position the plurality of sutures in the vessel wall.

Advancing the plurality of needles may include advancing a pair of needles through the anchor and separate pairs of needles on opposite sides of the anchor. The method may include retracting the anchor, and withdrawing the suture placement device may position the plurality of sutures extending across the puncture. Advancing the plurality of needles may include advancing the plurality of needles concurrently. The anchor may include first and second arms arranged opposite of each other, and separate needles may extend through the first and second arms when the anchor is in the expanded position. Retracting the plurality of needles may pull a portion of at least some of the plurality of sutures through the anchor.

The foregoing and other features, utilities, and advantages of the invention will be apparent from the following detailed description of the invention with reference to the accompanying drawings.

BRIEF DESCRIPTION OF THE DRAWINGS

FIG. 3A is a perspective view of a distal end portion of the vascular closure device of FIG. 1 extending through a vessel puncture.

FIG. 3B is a side view of a handle portion of the vascular closure device of FIG. 1 with actuator positions corresponding to a state of the distal end portion shown in FIG. 3A.

FIG. 4A is a perspective view of the distal end portion of the vascular closure device of FIG. 3A with the anchor in an extended position.

FIG. 4B shows actuator positions of the handle portion r corresponding to a state of the distal end portion shown in FIG. 4A.

FIG. 5A is a perspective view of the distal end portion of the vascular closure device of FIG. 4A with a portion of the vessel wall captured between the anchor and a body portion of the vascular closure system.

FIG. 5B shows actuator positions of the handle portion corresponding to a state of the distal end portion shown in FIG. 5A.

FIG. 5C is a side view of the distal end portion of the vascular closure device of FIG. 5A.

FIG. 6A is a perspective view of the distal end portion of the vascular closure device of FIG. 5A with needles extending through the vessel wall.

FIG. 6B shows actuator positions of the handle portion corresponding to a state of the distal end portion shown in FIG. 6A.

FIG. 7A is a perspective view of the distal end portion of the vascular closure device of FIG. 6A with the needles connected to sutures within the vessel.

FIG. 7B is a detailed inset showing connection of the needles to the sutures in FIG. 7A.

FIG. 8A is a perspective view of the distal end portion of the vascular closure device of FIG. 7A with the needles retracted partially.

FIG. 8B shows actuator positions of the handle portion corresponding to a state of the distal end portion shown in FIG. 8A.

FIG. 12 shows the sutures of FIG. 11 tied to close the vascular puncture.

FIG. 13 shows a pair of sutures tied to close the vascular puncture.

DETAILED DESCRIPTION

Figure 1:
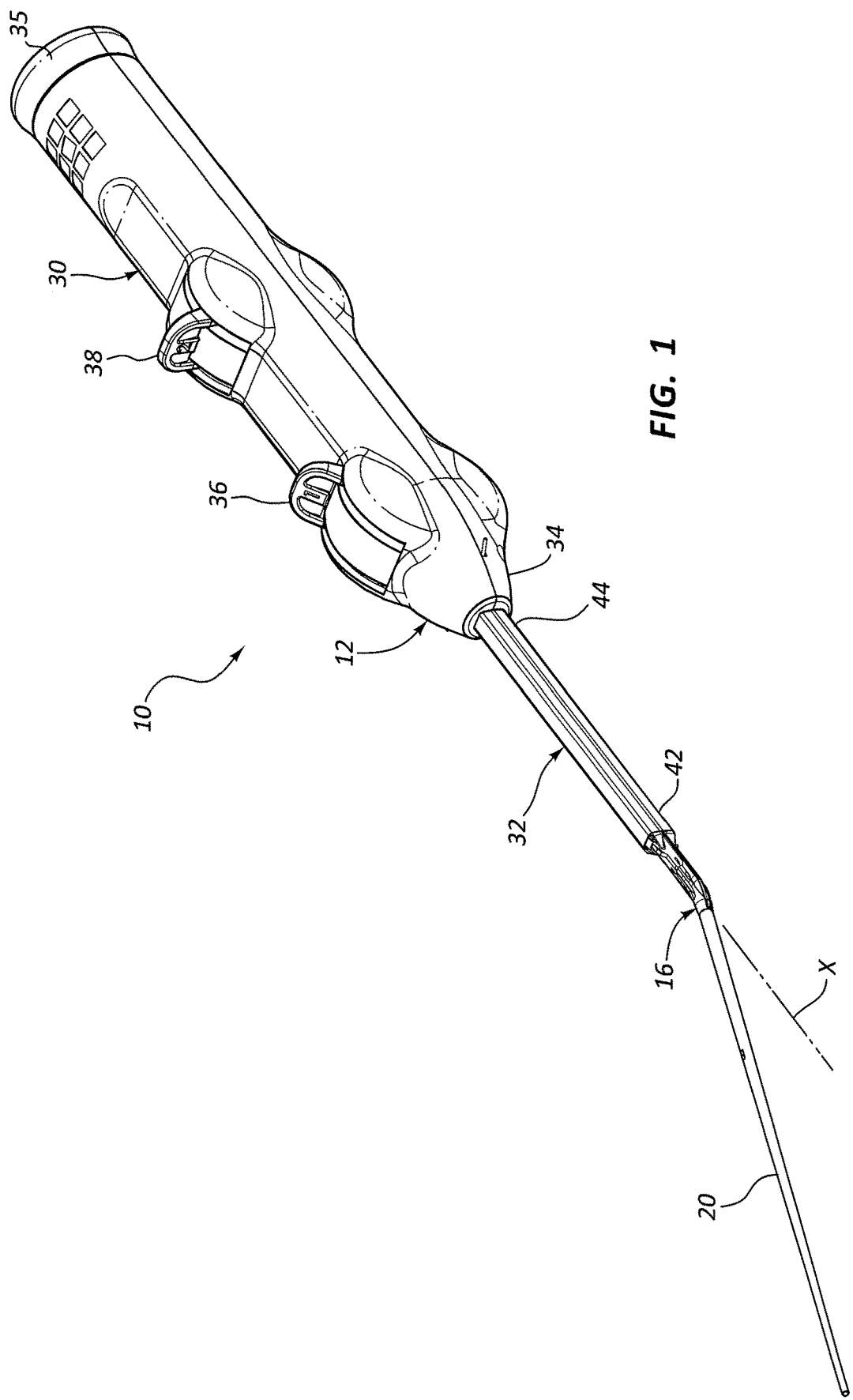
FIG. 1 is a perspective view of an example vascular closure device in accordance with the present disclosure.

The present disclosure is directed to devices and methods that place at least one suture across a wound (e.g., a puncture in a vessel). In one embodiment, the device is adapted and configured to place three sutures across an opening (e.g., vascular puncture) in a wall of the vessel. The present disclosure contemplates that a medical procedure will be performed through a sheath that is inserted through the opening in the vessel wall. The sheath provides access to the inside of the vessel. The device may be used prior to the sheath being inserted through the opening or after the medical procedure has been completed and the sheath removed. The device deploys at least one suture across the vessel opening by inserting a plurality of needles through the vessel wall adjacent to the opening. The needles grasp lengths of suture held by the device within the vessel. Withdrawing the needles pulls the lengths of suture through the vessel wall. The sutures may be subsequently used to close the opening. One use of the device is to place at least one suture through the vessel wall, wherein the suture is later used to close the opening in the vessel wall (e.g., a puncture in a femoral artery formed during a catheter-based procedure).

While the vascular instruments shown and described below include procedural sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

The devices and methods of the present disclosure may be particularly useful for suture-based closure of large bore openings. Large bore openings typically have a size of at least 10 French (F), such as in the range of about 10 F to about 24 F.

One aspect of the present disclosure relates to a vascular closure device that uses three pairs of needles to deliver three separate sutures. At least one of the pairs of needles extends through a portion of an anchor member of the vascular closure device. The pair of needles may extend through the anchor when the anchor is in an expanded or deployed position, such as when the anchor is used to capture a portion of a vessel wall between a body portion of the vascular closure device and a proximal contact surface of the anchor when the anchor is in a deployed position. The vascular closure device operates to position three sutures extending across a vessel puncture. The three sutures may then be used to seal the vessel puncture upon removal of the vascular closure device from the vessel puncture.

Another aspect of the present disclosure relates to a vascular closure device having at least one needle operable to extend through a portion of an anchor as part of positioning at least one suture across a vessel puncture. The at least one needle extending through the anchor may include a pair of needles that extend through a vessel wall on opposing sides of the vessel puncture. In one example, the vascular closure device may further include at least one needle that extends through the vessel wall at a location spaced apart from the anchor. In one example, separate pairs of needles extend through the vessel wall on opposite sides of the anchor when the anchor is in the expanded or deployed position to position separate sutures through the vessel wall on opposite sides of the anchor. The at least one needle extending through the anchor may position a separate suture extending through the vessel wall at a location in alignment with the anchor as a result of the at least one needle extending through a portion of the anchor.

Delivering a needle or pair of needles through the anchor when the anchor is in the deployed position may provide a more compact vascular closure device design by taking advantage of the otherwise unavailable portion of a width of the vascular closure device that is occupied by the anchor, which in previous designs was assumed to be unavailable space for operating a needle or pair of needles, and therefore unavailable for suture placement. For large bore vessel punctures, this leaves a significant portion of the vessel puncture lacking closure (e.g., coverage) by a suture.

Positioning a plurality of sutures (e.g., at least three sutures) across a vessel puncture using a vascular closure device may provide improved closure of the vessel puncture as compared to a method of closing a vessel puncture that includes positioning only a single suture or only a pair of sutures across the vessel puncture. Furthermore, delivering a suture across a vessel puncture at a position along the length of the vessel puncture that corresponds with (e.g., aligns with) a position of the anchor when the anchor is deployed may provide positioning of the suture at a position centrally along the length of the vessel puncture, which may provide improved closure of the puncture after removal of the vascular closure device.

The anchors disclosed herein may also be referred to as backboards, anchor portions, anchor legs, or anchor arms. The anchors may be moveable between a retracted position having a reduced profile for delivery through the vessel puncture, and an expanded position used to capture a portion of the vessel wall between the anchor, which is positioned internal the vessel, and a body portion of the vascular closure device, which is positioned external the vessel. After capturing a portion of the vessel wall using the expanded anchor, the plurality of needles may be advanced through the vessel wall. The needles connect to suture portions positioned internal the vessel, which are carried by a suture carrying a member of the vascular closure device. Withdrawing the needles after the needles have connected with the suture portions pulls the sutures through the vessel wall. Withdrawing the vascular closure device after withdrawing the needles positions the sutures extending across the vessel puncture. The sutures may then be tied or otherwise secured (e.g., using a suture locking device) to close the vessel puncture. In at least some arrangements, additional sealing material may be delivered to the vessel puncture along an outer surface of the vessel wall after closing the vessel puncture with the sutures. An example sealing material is a bioadhesive.

Figure 2:
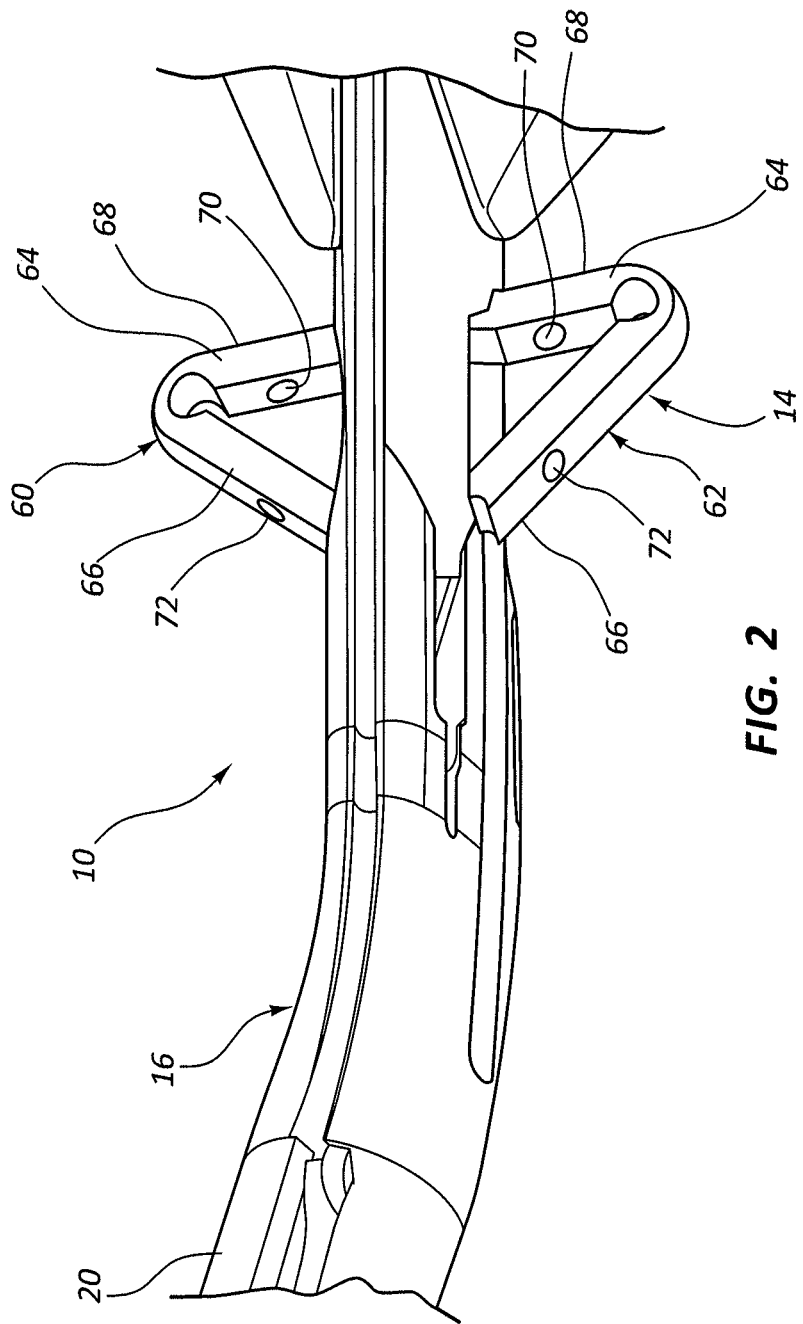
FIG. 2 is a perspective of an anchor of the vascular closure device of FIG. 1 in an expanded position.

Referring now to FIGS. 1 and 2, an example vascular closure device 10 is shown including a body portion 12, an anchor 14, a suture carrying portion 16, a plurality of needles 18 (see FIGS. 6A, 7A, 8A), and a distal locator tip 20. The body portion may include a handle 30 and a delivery portion 32. The anchor 14 may be expandable and retractable relative to the body portion 12 and suture carrying portion 16. The needles may be operable to move between a withdrawn position within the body portion 12, and an advanced position protruding through the vessel wall. The needles may be used to grasp lengths of suture carried by the suture carrying portion and, when withdrawn, pull the lengths of the sutures through the vessel wall adjacent to the vessel puncture. Operation of the vascular closure device 10 is shown and described in further detail with reference to FIGS. 3A-12.

The handle 30 of the body portion 12 includes distal and proximal ends 34, 35, and first and second actuators 36, 38. The first and second actuators 36, 38 may be pivotally mounted to the handle 30. Operation of the first actuator 36 moves the anchor 14 between retracted and extended positions. Typically, the anchor 14 maintains the retracted position while advancing the vascular closure device 10 through a vessel puncture in a vessel wall. The vascular closure device 10 may have its smallest outer profile when the anchor 14 is in the retracted position to promote insertion through the vessel puncture. The first actuator 36 may be rotated forward to expand or extend the anchor 14 into a position that limits removal of the vascular closure device 10 from the vessel. The anchor 14, when in the expanded or extended position, may be used to capture the vessel wall between a proximal contact surface of the anchor and a distal surface of the body portion in preparation for advancing the needles through the vessel wall.

The anchor 14 may be moveable axially relative to the body portion 12 when the anchor 14 is in the expanded position. Operation of the first actuator 36 through a first portion of its actuation path (e.g., through a first portion of its rotation path in a forward or advancing direction as shown in FIG. 4B) may move the anchor 14 between expanded and retracted positions (see FIGS. 3A-4B). Operation of the first actuator 36 through a second portion of its actuation path (e.g., through a second portion of its rotation path in a forward or advancing direction as shown in FIG. 5B) may move the expanded anchor axially in a rearward or proximal direction (e.g., withdraw the expanded anchor 14 proximally towards the body portion 12 as shown in FIGS. 5A-5C).

Figure 6C:
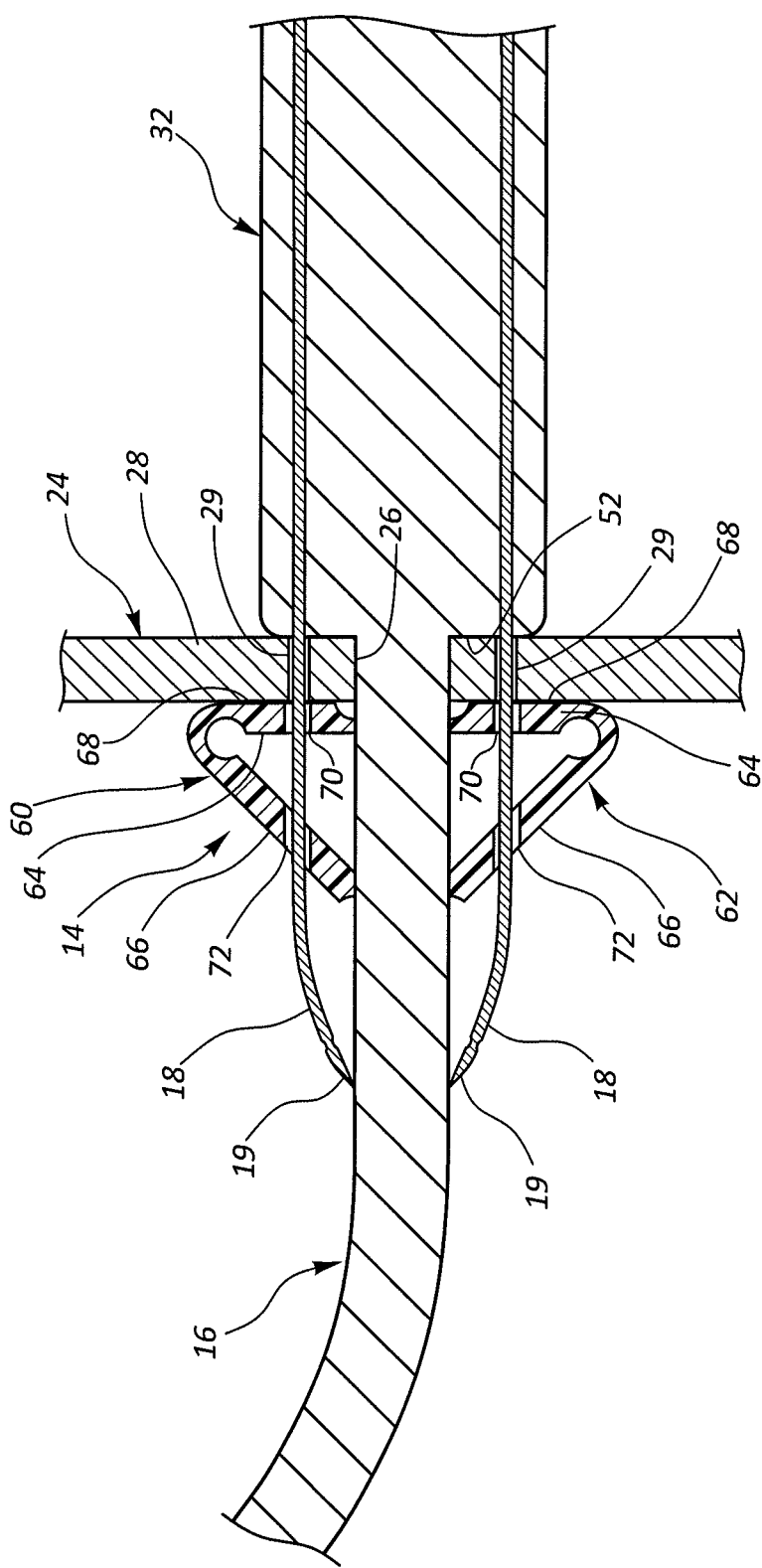
FIG. 6C is a schematic cross-sectional view of the vascular closure device shown in FIG. 6A.
Figure 9:
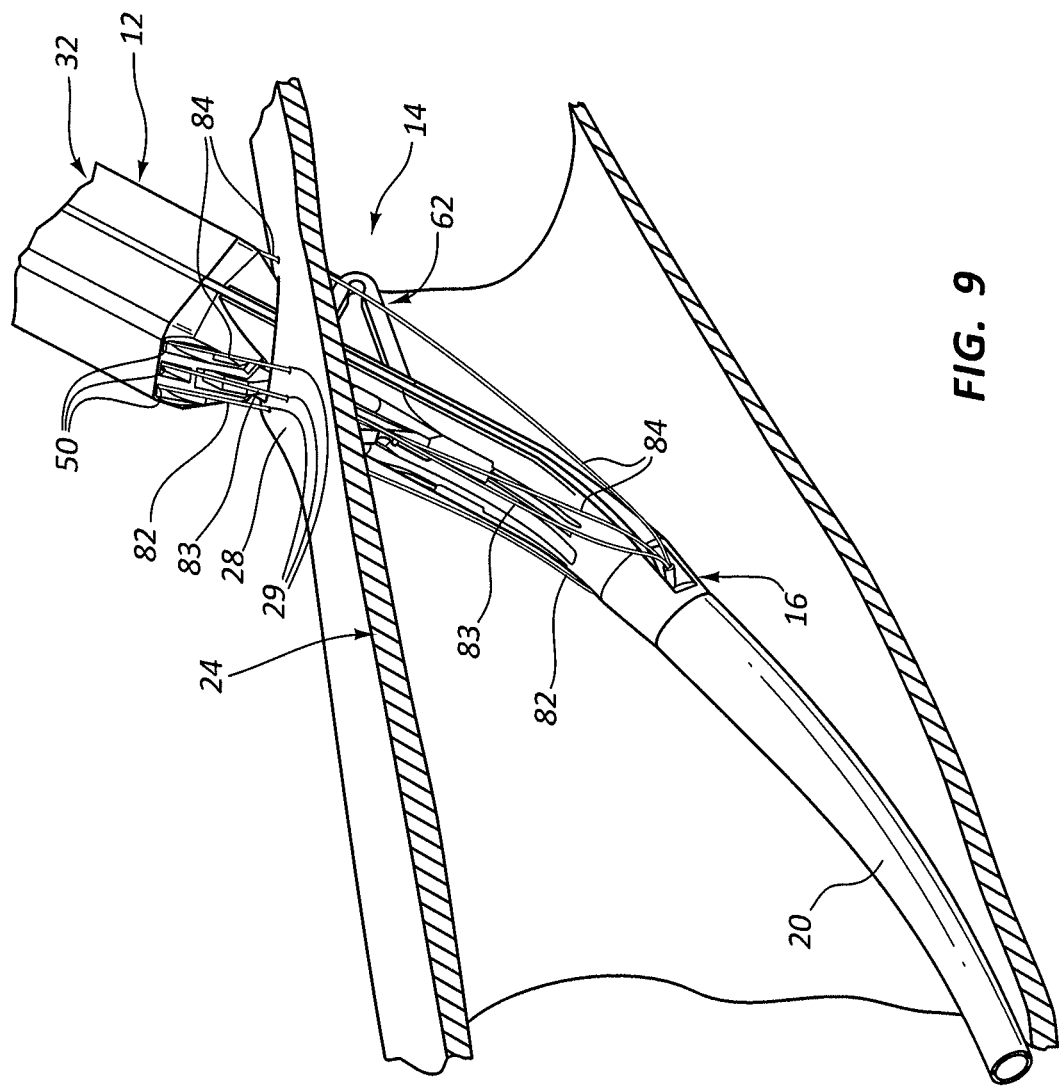
FIG. 9 is a perspective view of the distal end portion of the vascular closure device of FIG. 8A with the needles fully withdrawn and the sutures extending through the vessel wall.
Figure 10A:
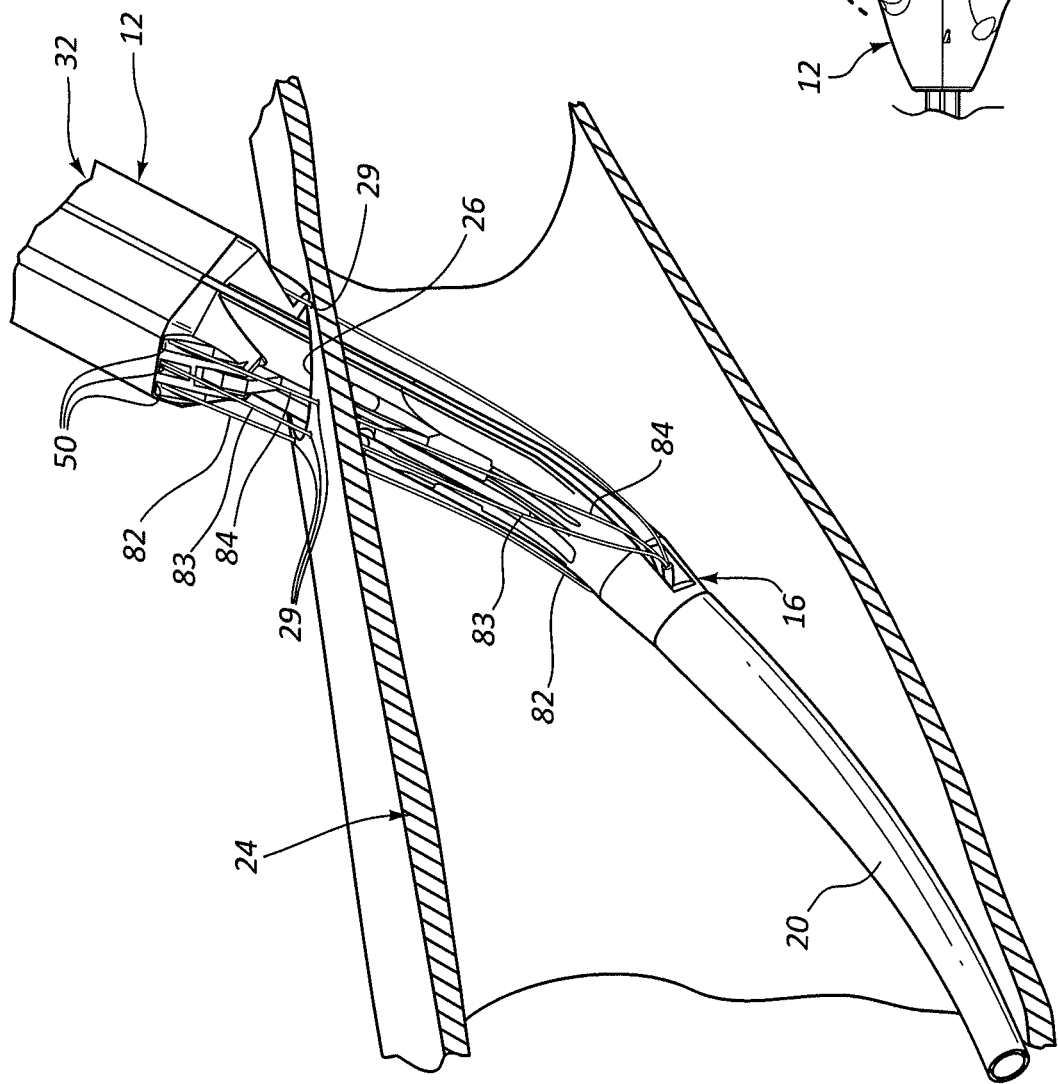
FIG. 10A is a perspective view of the distal end portion of the vascular closure device of FIG. 9 with the anchor in a retracted position.
Figure 10B:
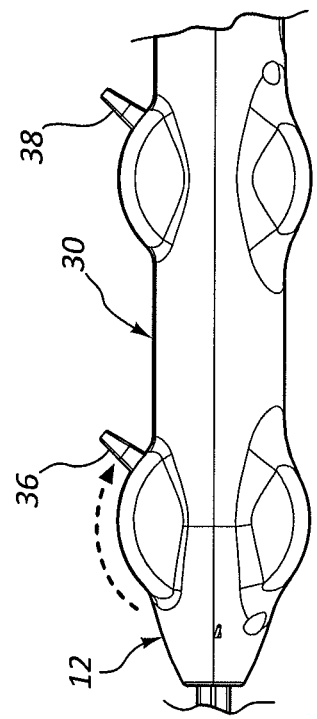
FIG. 10B shows the actuator positions of the handle portion corresponding to a state of the distal end portion shown in FIG. 10A.

The second actuator 38 may be operable to move the needles 18 between withdrawn and extended positions. The needles 18, when in a withdrawn position, may be completely recessed within the body portion 12. Operation of the second actuator 38 (i.e., rotation in a forward rotated direction as shown in FIG. 6B) advances the needles 18 distally out of the body portion 12 and through a vessel wall (see FIGS. 6A-6C). The needles 18 include distal needle tips 19 (see FIGS. 6B-6C) that connect to sutures 82-84 carried by the suture carrying portion 16. Once the needles 18 are connected to the sutures 82-84, the second actuator 38 is operated in a reverse rotation direction (see FIG. 8B) to withdraw the needles 18 back into the body portion 12 as shown in FIGS. 8A-9. Withdrawing the needles 18 proximally pulls the sutures 82-84 through the vessel wall. The anchor 14 is retracted by rotating the first actuator 36 in a reverse direction as shown in FIGS. 10A and 10B. Removing the vascular closure device 10 from the vessel puncture positions the sutures 82-84 extending across the vessel puncture.

Figure 11:
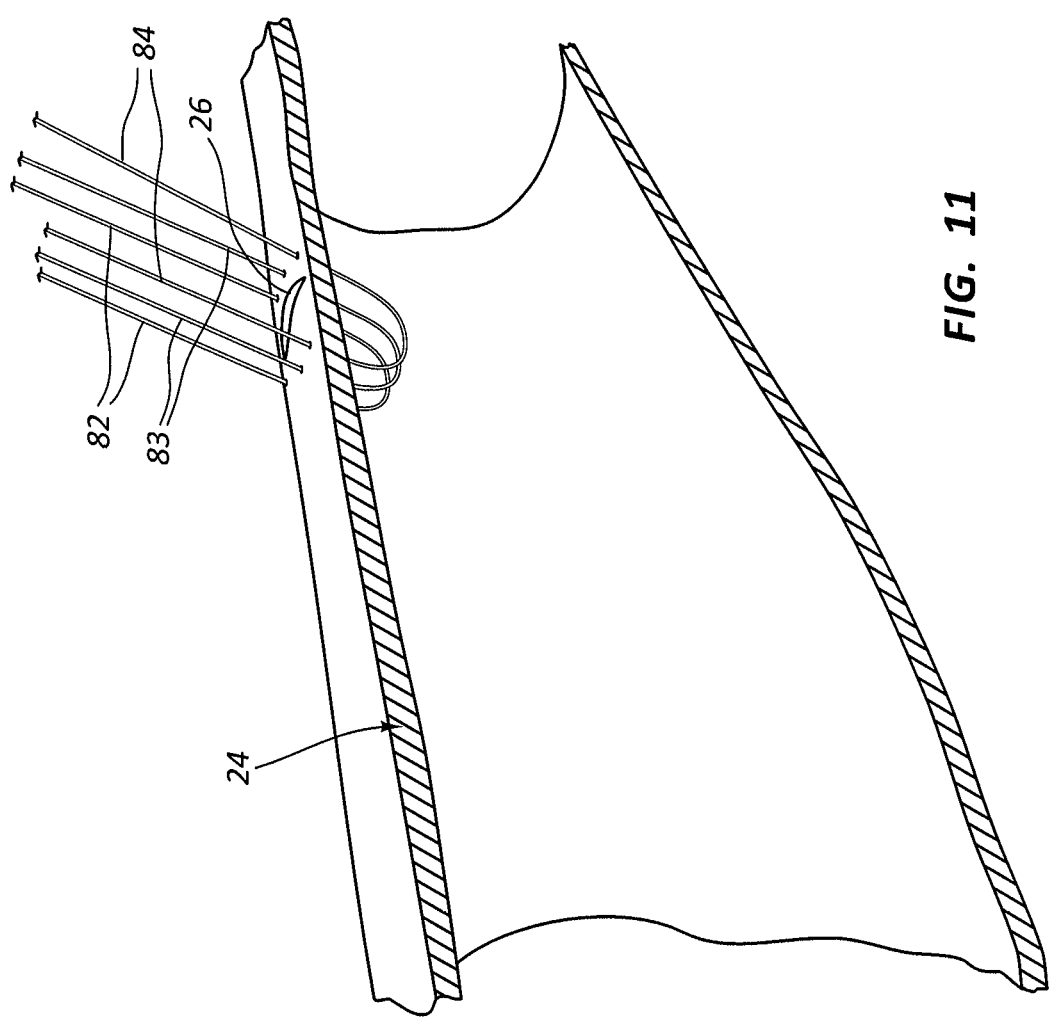
FIG. 11 shows the sutures extending across the vascular puncture upon removal of the vascular closure device.

Free ends of the sutures 82-84 are then exposed for handling by an operator outside of the patient as shown in FIG. 11. The operator may form a knot in the sutures or advance a suture locking device along the sutures to close the vessel puncture as shown in FIG. 12.

The body portion 12 may include, for example, biasing members, spools, linkages, and other features internal the handle 30 to assist in transferring the pivotal operation of the first and second actuators 36, 38 to operation of the anchor 14 and needles 18 between retracted or withdrawn positions and expanded or advanced positions. Details concerning internal features used to couple actuators on a handle to movement of distal features on a vascular closure device are disclosed in U.S. patent application Ser. No. 13/490,816 filed on 7 Jun. 2012, and entitled "Large Bore Closure Device and Methods," which application is incorporated herein in its entirety by this reference.

The delivery portion 32 of the body portion 12 includes distal and proximal ends 42, 44, a plurality of needle openings 50, and a distal end surface 52. The proximal end 44 of the delivery portion 32 is mounted to the handle 30. The suture carrying portion 16 extends from the distal end 42 of the delivery portion 32. The plurality of needles 18 may be advanced through and withdrawn into the needle openings 50. The needle openings 50 may be positioned adjacent to the distal end surface 52. The needle openings 50 may be positioned on opposite sides of the suture carrying portion 16, which may be the same side of the suture carrying portion 16 from which the anchor 14 extends.

The distal end surface 52 may define a contact surface against which a portion of a vessel wall is contacted when captured between the body portion 12 and anchor 14. A distal end surface 52 may include a generally flat, planar portion that extends substantially perpendicular to a longitudinal axis X of the body portion 12 (see FIG. 1).

The anchor 14 is moveable between a retracted position show in FIG. 1 and an expanded or extended position shown in FIG. 2. While in the retracted position, the vascular closure device 10 has a reduced profile that permits insertion of the anchor 14 through a tissue puncture. Upon actuation into an expanded or extended position, the anchor 14 resists removal of the vascular closure device 10 in a proximal direction back through the tissue puncture.

The anchor 14 may include first and second arms 60, 62, wherein each arm includes a contact segment 64 and a support segment 66. The contact segments 64 each include a contact surface 68 and a needle aperture 70. The support segments 66 each include a separate needle aperture 72. When the anchor 14 is in an expanded position as shown in FIG. 2, the needle apertures 70, 72 are aligned axially with each other such that one of the needles 18 may extend through the needle apertures 70, 72 and into contact with one of the sutures carried by the suture carrying portion 16.

The contact segment 64 may be arranged generally perpendicular to the longitudinal axis X when the anchor 14 is in the expanded position. The support segments 66 are typically arranged at an angled orientation and provide support for the contact segment 64. The contact surface 68 of the contact segments 64 is arranged facing the distal end surface 52 of the body portion 12. The contact surface 68 is arranged to contact an interior surface of a vessel wall when the vessel wall is captured between the body portion 12 and the expanded anchor 14.

The needle apertures 70, 72 may have any desired shape and size. The needle apertures 70, 72 are sized and arranged to receive one of the needles 18 in a generally axial or longitudinal direction. The needle apertures 70, 72 of each of the first and second arms 60, 62 may be arranged coaxial with each other along an axis that is arranged generally parallel to the longitudinal axis X. In other arrangements, the axis along with the needle aperture 70, 72 are aligned is oriented at an angle relative to the longitudinal axis X, such as a tapered angle that directs the needles 18 radially inward toward the suture carrying portion 16.

The needle aperture 70, 72 may be formed in the first and second arms 60, 62 using any desired method including, for example, drilling or forming (e.g., using a molding process). The needle apertures 70, 72 may be configured as pass-through bores through each of the contact and support segments 64, 66. Alternatively, the needle aperture 70, 72 may have access along one of the side or lateral surfaces of the contact and support segments 64, 66 as well as along the distal and proximal surfaces of the contact and support segments 64, 66 when the first and second arms 60, 62 are in the expanded position.

The anchor 14, when in the expanded position shown in FIG. 2, may be repositioned in an axial direction to capture a portion of a vessel wall 24 between the contact surface 68 and the distal end surface 52 as shown in FIGS. 5C and 6C. The anchor 14 may be moveable axially while the anchor 14 maintains the expanded position. In some arrangements, the anchor 14 moves into the expanded position while at the same time being repositioned in an axial direction to capture the vessel wall 24 between the anchor 14 and the body portion 12. The vessel wall 24 may be released by advancing the anchor 14 distally away from the body portion 12. In some arrangements, the anchor 14 may move into a retracted position concurrently with advancing the anchor 14 distally to release the vessel wall 24.

The anchor 14 may be configured to provide a maximum surface area at the contact surface 68 when the anchor 14 is in the expanded position. In some arrangements, the anchor 14 includes only a single arm, while in other arrangements the anchor includes three or more arms that each includes a contact surface 68. In one example, the anchor 14 extends distally out of the body portion 12, while in other arrangements at least a portion of anchor 14 extends radially outward from the suture carrying portion 16 or other structure that is positioned distal of the body portion 12. Each arm, or only a select number arms, of the anchor may include at least one of the needle apertures 70, 72 discussed herein.

Any one of the anchor arms (e.g., first and second arm 60, 62) may include at least one aperture sized and arranged to permit one of the needles 18 to pass there through. Regardless of the position of the anchor 14 relative to the body portion 12 and suture carrying portion 16, the space occupied by the anchor when in the expanded position may be utilized for advancing a needle there through to position a suture across a vessel puncture at a location in which the anchor contacts the vessel wall adjacent to the vessel puncture.

The suture carrying portion 16 may include an anchor slot 74, a needle receiving slot 76, a suture slot 78, and suture connectors 80. The suture carrying portion 16 may carry or support at least portions of the sutures 82-84. For example, the suture carrying portion 16 may support three ends of the sutures 82-84, which each have a suture connector 80 mounted thereto. A length of the sutures 82-84 extending between the free ends of each suture may extend internally along the suture carrying portion 16 and body portion 12 and into the handle 30. When withdrawing the vascular closure device 10 from the vessel puncture after pulling the free ends of the sutures through the vessel wall, the length of the suture between the free ends is pulled out of the handle 30, body portion 12 and suture carrying portion 16 to position a continuous length of the sutures 82-84 across the vessel puncture.

The needle receiving slots 76 may be constructed as grooves or recesses along a length dimension of the suture carrying portion 16. Distal needle tips 19 of the needles 18 may extend into the needle receiving slot 76 to guide the needles 18 into the suture connectors 80 as shown in FIG. 6A. The anchor slot 74 provides a space within which the anchor 14 resides until moved into the expanded position. The distal locator tip 20 extends distally from the suture carrying portion 16. The distal locator tip 20 may provide a flexible leading portion of the vascular closure device that improves ease of insertion through a vessel puncture and along a length of an internal lumen of the vessel.

A vessel wall 24 of a vessel may include a vessel puncture 26 as shown in FIG. 3A. The needles 18 form a plurality of needle openings 29 positioned adjacent to the vessel puncture 26. The needle openings 29 may be positioned radially outward (e.g., laterally relative to a longitudinal axis of the device) and spaced apart from the vessel puncture 26. Typically, the vessel puncture 26 is generally elongate having opposite sides that define a length of the puncture and opposing ends of the puncture. The sutures 82-84 may extend across the vessel puncture 26 from one side to an opposite side as shown in FIG. 12.

Free ends of the sutures 82-84 extend through the suture slot 78 and are coupled to the suture connectors 80. Connecting the suture connectors 80 to the needles 18 couples the sutures 82-84 to the needles 18. Typically, a separate needle 18 is connected to a separate end of each of the sutures 82-84 via the suture connectors 80.

The sutures 82-84 may extend at least partially within the needle receiving slots 76. Additional length of the sutures 82-84 may extend internally within the suture carrying portion 16, the body portion 12 and handle 30, as described above.

Upon connection of the needles 18 to the suture connectors 80, the needles 18 may be withdrawn proximally to pull the sutures 82-84 through the vessel wall 24 (e.g., the needle openings 29) at a location adjacent to the vessel puncture 26.

The suture connectors 80 may include a wire loop at one end for connection to a needle 18, and include a suture connection feature at opposing end for connection to a free end of one of the sutures 82-84. The needles 18 may include latch, hook, barb or other features that provide a positive connection between the needles 18 and the suture connectors 80. Other constructions and configurations are possible for the suture connectors 80 to provide a positive connection, either releasable or permanent, between the needles 18 and the sutures 82-84.

The needles 18 include a distal needle tip 19 as described above. When the needles 18 are advanced by activation of the second actuator 38, the distal needle tips 19 extend through the vessel wall 24 and into the needle receiving slot 76 (see FIG. 6A). Further advancing the needles 18 connects the distal needle tips 19 to the suture connectors 80 as shown in FIGS. 7A and 7B. Withdrawing the needles 18 proximally by actuation of the second actuator 38 (see FIG. 8B) draws the sutures 82-84 through the needle openings 29 in the vessel wall 24 as shown in FIGS. 8A and 9. Withdrawing the vascular closure device 10 places the sutures 82-84 across the vessel puncture 26 as shown in FIG. 11.

The vessel wall aligned portion 28 may include that portion of the vessel wall 24 which is captured between the contact surface 68 of the anchor 14 and the distal end surface 52 of the body portion 12 (see FIGS. 5A and 5C). The body portion 12 is typically inserted through the vessel wall 24 at an angle relative to an outer surface of the vessel wall 24 and at an angle relative to a longitudinal axis Y of the vessel as shown in FIG. 5C. The angle of insertion may be an angle $A_3$, which is a combination of angles $A_1$ and $A_2$ shown in FIG. 5C. The vessel wall aligned portion is arranged at a perpendicular angle $A_1$ relative to the longitudinal axis X of the body portion 12. Providing the vessel wall aligned portion 28 at the perpendicular angle $A_1$ may provide improved consistency in placing the needle openings 29 relative to the vessel puncture 26 when inserting the needles 18.

As the needles 18 are advanced by actuating the second actuator 38, the needles 18 protrude at a perpendicular angle relative to the vessel wall aligned portion 28. The needles 18 are shown in at least FIG. 6A arranged at a non-perpendicular angle relative to the remaining portions of the vessel wall 24. Typically, the body portion 12 is inserted at an angle $A_3$, which is usually about 90° and preferably in the range of about 80° degrees to about 100°. In some arrangements, the insertion angle $A_3$ is about 90° so that the vessel wall 24 and vessel wall aligned portion 28 are arranged generally in parallel.

Referring now to FIG. 12, the sutures 82-84, which positioned across the vessel puncture 26 by operation of the vascular closure device 10, have knots 86 formed therein to maintain tension across the vessel puncture 26 to hold the vessel puncture 26 closed. The suture 83 is positioned spaced between the sutures 82, 84. The suture 83 may be positioned generally at a mid-point along the length of the vessel puncture 26. The suture 83 may be positioned across the vessel puncture 26 by advancing needles 18 through the first and second arms 60, 62 of the anchor 14.

In other examples, the vascular closure device may include only one pair of needles, wherein the single pair of needles extends through the first and second arms 60, 62 to position the suture 83 at a mid-point along the length of the vessel puncture. Other arrangements are possible in which more than one suture is placed across the vessel puncture and at least one needle of the vascular closure device extends through at least a portion of the anchor. FIG. 13 shows placement of a pair of sutures using a vascular closure device having two pairs of needles. Any one of the needles used to position the sutures 82-84 shown in FIG. 13 may extend through at least a portion of an anchor (e.g., an anchor arm) of the vascular closure device.

The anchor of the vascular closure device may be aligned with a mid-point along a length of the vessel puncture such that a suture placed by advancing a needle through a portion of the anchor is also positioned at approximately a mid-point along the length of the vessel puncture (e.g., see suture 83 in FIG. 12). Other arrangements may provide positioning of the anchor at other locations along the length of the vessel puncture such that advancing a needle through a portion of the anchor to position a suture through the vessel wall places the suture at a location spaced away from the mid-point along a length of the vessel puncture, such as the position of one of the sutures 82, 84 shown in FIG. 13.

At least FIG. 3A of the present disclosure shows a needle receiving slot 76 arranged to receive a needle passing through the first arm 60, wherein the needle receiving slot 76 is positioned adjacent to (e.g., laterally next to) the anchor slot 74. In other arrangements, the needle receiving slot 76 is arranged to receive a needle passing through an arm of the anchor is positioned coaxially with the anchor slot 74 such as, for example, at a distal end of the anchor slot 74 or positioned distally of the anchor slot 74.

As used in this specification and the appended claims, the terms "engage" and "engagable" are used broadly to mean interlock, mesh, or contact between two structures or devices. A "tube" is an elongated device with a passageway. A "lumen" refers to any open space or cavity in a bodily organ, especially in a blood vessel. The words "including"

and "having," as well as their derivatives, as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A vascular closure device, comprising:
an anchor positionable through a vessel puncture in a vessel wall and configured to move between an expanded position and a contracted position, the anchor defining a plurality of apertures aligned along an axis that is parallel to a longitudinal axis of the vascular closure device when the anchor is in the expanded position;
at least three needles positionable external to the vessel puncture in the vessel wall;
at least three sutures positionable within the vessel puncture and the vessel wall;
a delivery device operable to advance the at least three needles through the vessel wall, to connect the at least three needles to the at least three sutures, and to withdraw the at least three needles and the at least three sutures through the vessel wall with the at least three sutures being parallel to each other;
wherein at least one needle of the at least three needles is configured to advance through the plurality of apertures in the anchor when the anchor is in the expanded position.

2. The vascular closure device of claim 1, wherein the delivery device comprises a body portion, the anchor, and a suture carrying portion, the at least three needles being advanceable from the body portion through the vessel wall and connectable to the at least three sutures while the at least three sutures are carried by the suture carrying portion and while the anchor is in the expanded condition.

3. The vascular closure device of claim 1, wherein the delivery device is operable to advance the at least three needles through the vessel wall with a line intersecting the at least three needles at an external surface of the vessel wall.

4. The vascular closure device of claim 1, wherein the at least three needles are movable through at least three aligned openings in the delivery device.

5. The vascular closure device of claim 1, wherein the delivery device is operable to withdraw the at least three sutures through the vessel wall with the at least three sutures crossing the vessel puncture internal to the vessel wall.

6. The vascular closure device of claim 1, wherein free ends of the at least three sutures are exposed for handling by an operator outside of the vessel wall upon the at least three sutures being positioned crossing the vessel puncture.

7. A vascular closure device, comprising:
an anchor positionable through a vessel puncture in a vessel wall and configured to move between an expanded position and a contracted position, the anchor defining at least two apertures aligned along an axis that is parallel to a longitudinal axis of the vascular closure device when the anchor is in the expanded position;
at least one needle movable through the at least two apertures of the anchor;
a body portion having a center plane dividing the body portion into a first side and a second side, the first side having at least one needle opening;
a suture carrying portion insertable through the vessel wall and configured to carry at least one suture to a position opposite the at least one needle opening relative to the vessel wall, wherein the at least one needle is movable through the at least one needle opening to connect to the at least one suture.

8. The vascular closure device of claim 7, further comprising a needle guide extending along a length dimension of the suture carrying portion, at least one needle being movable within the needle guide.

9. The vascular closure device of claim 8, wherein the needle guide comprises at least one slot.

10. The vascular closure device of claim 7, wherein the vascular closure device further comprises a second needle movable through the second side of the body portion.

11. The vascular closure device of claim 7, wherein the suture carrying portion comprises a suture slot configured to receive the at least one suture.

12. The vascular closure device of claim 7, wherein the suture carrying portion comprises an anchor slot, a portion of the anchor being movable between a first position within the anchor slot and a second position extending from the anchor slot.

13. A vascular closure device, comprising:
an anchor positionable through a vessel puncture in a vessel wall and operable between an expanded position and a contracted position, the anchor defining a plurality of apertures arranged along an axis that is parallel to a longitudinal axis of the vascular closure device when the anchor is in the expanded position;
a body portion having an upstream-facing side and a downstream-facing side upon insertion through a vascular opening;
a suture carrying portion extending distal to the body portion, the suture carrying portion having an upstream-facing side and a downstream-facing side;
a set of sutures carried on the upstream-facing side or downstream-facing side of the suture carrying portion;
a set of at least three needles movable through the upstream-facing side or downstream-facing side of the body portion to connect to the set of sutures, at least one needle of the set of at least three needles movable through the plurality of apertures of the anchor in the expanded position.

14. The vascular closure device of claim 13, wherein the set of at least three needles extends through at least three openings in the body portion.

15. The vascular closure device of claim 14, wherein the at least three openings are aligned on the body portion.

16. The vascular closure device of claim 13, further comprising a set of suture connectors carried on the suture carrying portion, wherein the set of at least three needles are connectable to the set of sutures via the set of suture connectors.

17. The vascular closure device of claim 13, wherein the anchor is positioned between the body portion and the set of sutures.

18. The vascular closure device of claim 13, wherein the anchor comprises a first portion residing in the upstream-facing side of the suture carrying portion and a second portion residing in the downstream-facing side of the suture carrying portion.

* * * * *